United States Patent

Idaomi et al.

Patent Number: 5,855,560
Date of Patent: Jan. 5, 1999

[54] CATHETER TIP ASSEMBLY

[75] Inventors: Michael Idaomi, Sunnyvale; Russell B. Thompson, Los Altos; Fernando Pumares, San Bruno, all of Calif.

[73] Assignee: EP Technologies, Inc., Sunnyvale, Calif.

[21] Appl. No.: 414,620

[22] Filed: Mar. 31, 1995

Related U.S. Application Data

[63] Continuation-in-part of Ser. No. 410,556, Mar. 23, 1995, which is a continuation of Ser. No. 55,138, Apr. 29, 1993, abandoned, which is a division of Ser. No. 790,203, Nov. 8, 1991, Pat. No. 5,257,451.

[51] Int. Cl.$^6$ ........................................................ A61B 5/00
[52] U.S. Cl. .............................. 600/585; 604/45; 604/46; 604/280; 600/433; 600/434
[58] Field of Search ...................................... 128/657, 658, 128/772; 604/280, 287, 282, 95, 96

[56] References Cited

U.S. PATENT DOCUMENTS

| | | |
|---|---|---|
| 3,612,058 | 10/1971 | Ackerman . |
| 4,763,647 | 8/1988 | Gambale . |
| 4,920,980 | 5/1990 | Jackowski ................................ 128/786 |
| 5,001,825 | 3/1991 | Halpern ................................... 128/772 |
| 5,106,381 | 4/1992 | Chikama .................................. 128/772 |
| 5,231,989 | 8/1993 | Middleman . |
| 5,238,005 | 8/1993 | Imran . |
| 5,255,668 | 10/1993 | Umeda .................................... 600/146 |
| 5,336,182 | 8/1994 | Lundquist et al. . |
| 5,363,861 | 11/1994 | Edwards et al. . |
| 5,431,168 | 7/1995 | Webster, Jr. ............................. 128/658 |
| 5,497,784 | 3/1996 | Imran ...................................... 128/772 |

FOREIGN PATENT DOCUMENTS

| | | |
|---|---|---|
| WO80/02231 | 10/1980 | WIPO . |
| WO91/11213 | 8/1991 | WIPO . |

*Primary Examiner*—Max Hindenburg
*Assistant Examiner*—Pamela Wingood
*Attorney, Agent, or Firm*—Lyon & Lyon LLP

[57] ABSTRACT

An electrode tip assembly for a catheter is bendable under the control of the user. The distal tip portion of the assembly is progressively less resistant to bending than the remaining portions. The variable stiffness is provided by tapering the width or thickness of a bendable spring component or otherwise providing a progressive change in bending characteristics by notching, dimpling or stepping the thickness of the spring.

11 Claims, 4 Drawing Sheets

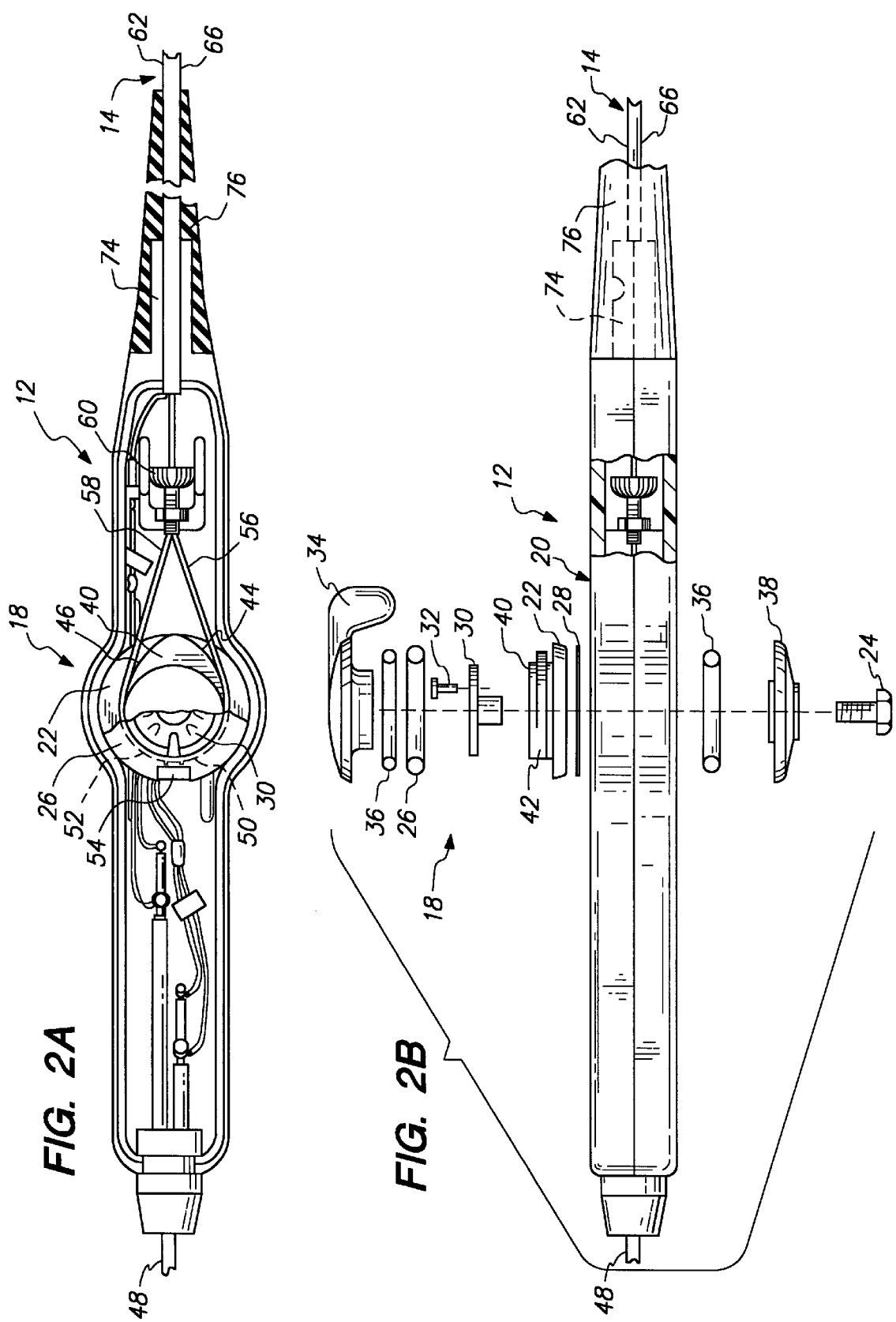

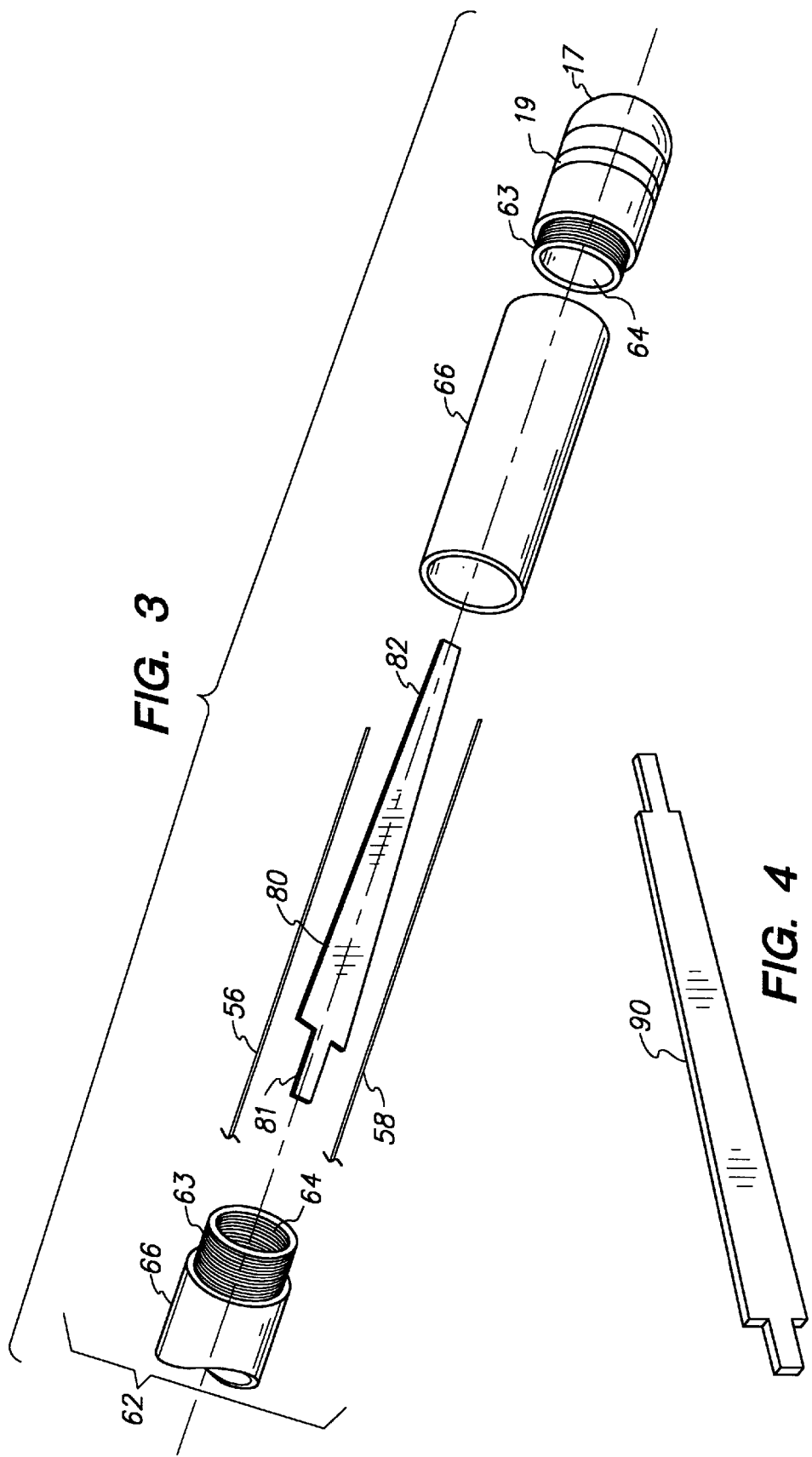

CATHETER TIP ASSEMBLY

RELATED APPLICATION

This application is a continuation in part of Ser. No. 08/410,556 filed Mar. 23, 1995, which is a continuation of application Ser. No. 08/055,138 filed Apr. 29, 1993, now abandoned, which is a division of Ser. No. 07/790,203 filed Nov. 8, 1991, now U.S. Pat. No. 5,257,451.

FIELD OF THE INVENTION

The invention generally relates to steerable catheters. In a more specific sense, the invention relates to catheters used for medical purposes that can be steered and manipulated within interior regions of the body from a location outside the body.

BACKGROUND OF THE INVENTION

Physicians make widespread use of catheters today in medical procedures to gain access into interior regions of the body. In its important that the physician can control carefully and precisely the movement of the catheter within the body. Steerable catheters using a bendable spring in the catheter distal tip are disclosed in U.S. Pat. No. 5,363,861 issued Nov. 15, 1994. The present invention relates to improvements and refinements of the devices disclosed therein.

The need for careful and precise control over the catheter is especially critical during procedures that ablate tissue within the heart. These procedures, called electrophysiological therapy, are becoming more widespread for treating cardiac rhythm disturbances. Such control can be improved by providing catheter distal tip steering assemblies having smoothly curving or otherwise carefully controllable curvatures upon deflection or bending.

During these procedures, a physician steers a catheter through a main vein or artery (typically the femoral) into the interior region of the heart that is to be treated. The physician then further manipulates a steering mechanism to place the electrode carried on the tip of the catheter into direct contact with the tissue that is to be ablated. The physician directs radio frequency energy into the electrode tip to ablate the tissue and form a lesion.

Cardiac ablation especially requires the ability to precisely bend and shape the tip end of the catheter to position the ablation electrode.

SUMMARY OF THE INVENTION

The invention provides an electrode tip assembly for a catheter that is bendable under the control of the user. In accordance with a preferred embodiment of the invention a stiffening mechanism is provided with an improved bendable lead spring which is progressively more resistant to bending along its length, preferably progressing in a proximal direction. This variable stiffness directs bending into improved curvature patterns and minimizes abrupt changes in curvature.

In a preferred embodiment, the electrode tip assembly includes an interior body bendable in response to external forces that has a uniform thickness but tapers in width, moving distally. The body is subjected to controlled external bending forces by at least one and preferably two steering wires that are attached to the body. One end of the body attaches to the guide tube of a catheter. The other end portion is adjacent to or attached to the tip electrodes.

The stiffening mechanism varies the stiffness of the body between its end portions so that the proximal end portion which is attached to the catheter is more resistant to bending than the distal end portion adjacent the tip electrode assembly. In this way, bending forces are distributed so as to form a smoother distal curve at the tip of the assembly, where the electrodes are located than was heretofore attainable.

In a further embodiment, the stiffening mechanism includes a spring that possesses a uniform width, but tapers in thickness. In accordance with yet a further embodiment both the width and thickness can be made to taper in the event that a more rapid progression in bending resistance is desired.

In accordance with still further embodiments of the invention the bending characteristics of a spring in a steering mechanism is varied incrementally by reducing the width thereof in a step wise fashion to effectively achieve a tapering effect. In accordance with a still further embodiment notches may be cut along the edges of a flat spring. In order to vary the bending characteristics of such a spring the frequency, width and depth of the notches can be varied incrementally to impart variable stiffness to the spring.

In accordance with yet another variation of the invention a specified length of a flat spring can be provided with dimples which tend to impart column stiffness thus increasing the resistance of the center support against axial buckling. The distal section, however is left in an undimpled state which is thus weaker and thus bending and axial loads are transferred to such distal portion.

Still further aspects advantages and objects of the invention will be apparent from the accompanying detailed description and claims together with the accompanying drawings.

BRIEF DESCRIPTION OF THE DRAWINGS

FIG. 2A is a side section view of the catheter taken generally along line 2A—2A in FIG. 1;

FIG. 2B is an exploded view of FIG. 2A;

FIG. 3 is an exploded view of a distal tip assembly of a catheter in accordance with a preferred embodiment of the invention;

FIG. 4 is a perspective view of a steering spring in accordance with the invention;

DESCRIPTION OF THE PREFERRED EMBODIMENT

Figure 1:
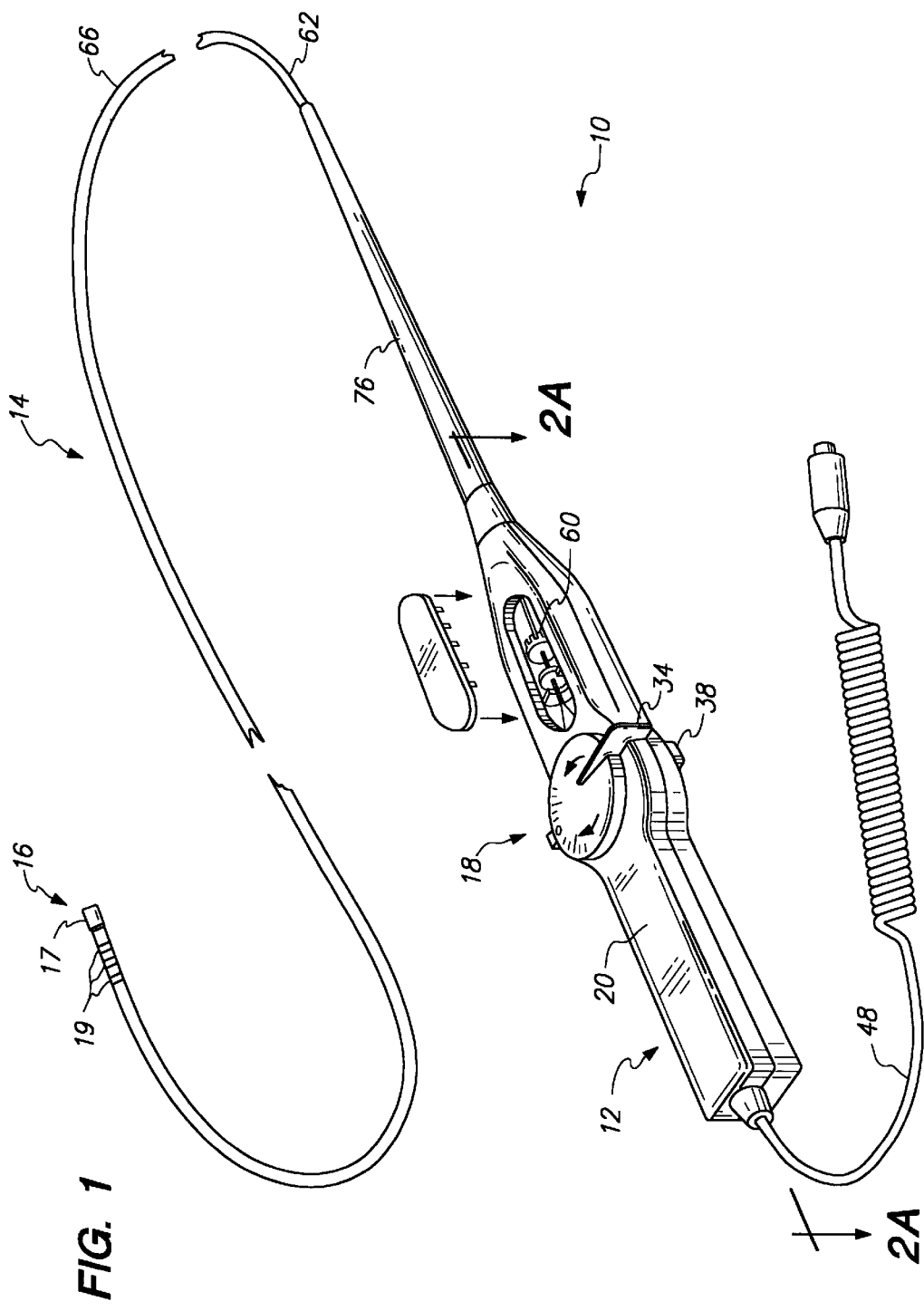
FIG. 1 is a perspective view of a catheter that embodies the features of the invention.

FIG. 1 shows the assembly of a steerable catheter 10 that embodies the features of the invention. As there shown, the catheter 10 includes three main parts or assemblies: the handle assembly 12, the guide tube assembly 14, and the electrode tip assembly 16 which usually includes at least one tip electrode 17 and one or more ring electrodes 19.

The catheter 10 can be used in many different environments. This specification will describe the catheter 10 as used to provide electrophysiologic therapy in the interior regions of the heart.

When used for this purpose, a physician grips the handle assembly 12 to steer the guide tube assembly 14 through a main vein or artery (which is typically the femoral arterial)

into the interior region of the heart that is to be treated. The physician then further manipulates a steering mechanism 18 on the handle assembly 12 (which will be described later) to place the electrode tip assembly 16 in contact with the tissue that is to be ablated. The physician directs radio frequency energy into the electrode tip assembly 16 to ablate the tissue contacting the electrode tip assembly 16.

As FIGS. 2A and 2B best show, the handle assembly 12 includes a housing 20 that encloses the steering mechanism 18. The specific steering mechanism 18, shown for purposes of illustration, includes a rotating cam wheel 22 carried on a screw 24 within the housing 20. The cam wheel 22 is seated for rotation between a top washer 26 and a bottom washer 28. A lock nut 30 and a pin 32 couple an external steering lever to the top of the cam wheel 22. The steering lever 34 seats against an O-ring 36.

Movement of the steering lever 34 by the user rotates the cam wheel 22 about the screw 24 within the housing 20. Clockwise movement of the steering level rotates the cam wheel 22 to the right. Counterclockwise movement of the steering wheel rotates the cam wheel 22 to the left. Contact between the steering lever 34 and the side of the housing 20 physically limits the range of left and right rotation of the cam wheel 22 within the housing 20.

The steering mechanism 18 also includes an external locking lever 38 that an adhesive couples to the head of the screw 24. The locking lever 38 seats against another O-ring 36.

Movement of the locking lever 38 rotates the screw 24. Clockwise rotation of the locking lever 38 tightens the screw 24 to increase the seating force between the cam wheel 22 and the bottom washer 28. When moved fully clockwise into contact against the housing 20, the locking lever 38 imposes a seating force that prevents rotation of the cam wheel 22 by the steering lever 34. Counterclockwise movement of the locking lever 38 loosens the screw 24 to decrease the seating force and free the cam wheel 22 for rotation.

The cam wheel 22 includes a forward cam face 40 and a rear cam face 42. The forward cam face 40 is oriented toward the front of the housing 20, where the guide tube assembly 14 attaches. The forward cam face includes a right side surface 44 and a left side surface 46.

The rear or proximal cam face 42 is oriented toward the back of the housing 20, where a coaxial cable 48 attaches. The rear cam face includes right and left side surfaces 50 and 52.

The cam wheel 22 also carries a wire fastener 54 between the right and left side surfaces 50 and 52 of the rear cam face 42. The wire fastener 54 holds the proximal ends of right and left catheter steering wires 56 and 58, which are soldered to the interior of the fastener 54.

The steering wires 56 and 58 extend from the opposite ends of the fastener 54 and along the associated left and right side surfaces 44/46 and 50/52 of the front and rear cam faces 40 and 42. The steering wires exit the front of the housing 20 through the interior bore of a tension screw assembly 60.

As will be described in greater detail later, the distal ends of the steering wires 56 and 58 are attached to the electrode tip assembly 16. They extend from the wire fastener 54 through the guide tube assembly 14 to the electrode tip assembly 16.

As also will be described in greater detail, the wire fastener 54 in association with the cam faces 40 and 42 translate rotation of the cam wheel 22 into lateral pulling movement of the steering wires 56 and 58 attached to the electrode tip assembly 16.

By rotating the cam wheel 22 to the left (by moving the steering lever 34 counterclockwise), the left steering wire 58 bears against the left front and rear cam surfaces 46 and 52. The cam surfaces 46 and 52 tension the left steering wire 58 to impose a discrete, constant pulling force that causes the electrode tip assembly 16 to bend to the left.

Also, by rotating the cam wheel 22 to the right (by moving the steering lever 34 clockwise), the right steering wire 56 bears against the right front and rear cam surfaces 44 and 50. The cam surfaces 44 and 50 tension the right steering wire 56 to impose a discrete, constant pulling force that causes the electrode tip assembly 16 to bend to the right.

Rotation of the tension screw assembly 60 additionally varies the amount of slack (i.e., tension) in the steering wires 56 and 58 between the wire fastener 54 and the distal ends of the steering wires 56 and 58. This controls the responsiveness of the electrode tip assembly 16 to rotation of the cam wheel 22.

The component parts of the handle assembly 12 can be constructed of various materials, depending upon the durability needed and the sterilization process used.

For example, when EtO (ethylene oxide) sterilization is used, the housing 20 and bottom washer 28 can be made of a polycarbonate material. In this arrangement, the cam wheel 22, steering lever 34, and locking lever 38 can be made of a Delrin material. These plastic materials are durable and EtO sterilizable. In this assembly, the lock nut 30, pin 32, and screw 24 are preferably made of a metallic material like brass or stainless steel.

As FIGS. 2–3 show, the guide tube assembly 14 includes a flexible tubular body 62 attached to the handle assembly 12. The flexible body 62 encloses an interior bore 64. The steering wires 56 and 58 pass through the interior bore 64.

The body 62 may be constructed in various ways. In one embodiment the body 62 comprises a length of stainless steel coiled into a flexible spring 63 enclosing the interior bore 64. A sheath 66 of plastic material encloses the coil. The sheath 66 is made from a plastic material, such as a polyolefin.

The handle assembly 12 includes a tubular stem 74 though which the proximal end of the guide tube assembly 14 extends for attachment to the tension screw assembly 60. The guide tube assembly 14 can be made in various lengths, often about 100 cm in length.

The electrode tip assembly 16 includes a bendable main support wire or lead spring 80 having left and right faces. In the illustrated embodiment, the lead spring 80 can be made of stainless steel flat wire stock in an elongated shape about 0.036 inch wide tapering down to about 0.025 inch at its distal end and about 0.015 inch thick. The lead spring 80, is about 3 inches in total length.

One or both of the opposite ends of the main lead spring 80 are cut away to form stepped shoulders resulting in a proximal tab 81. In the illustrated embodiment, the tab 81 is about 0.013 inch wide and aligned along the centerline of the lead spring 80. Tab 81 is about 0.12 inch in length.

As FIG. 3 shows, stepped tab 81 fits within the distal end of the flexible guide tube body 62 to append the electrode tip assembly 16 to the guide tube assembly 14. The shoulders of tab 81 serve to center the lead spring 80 relative to the flexible guide tube body 62. Tab 81 has the further effect of constraining the side to side flexing of spring 80 insuring that the flexing remains planar (ie., perpendicularly to the central plane of spring 80) thus maximizing the reliability and accuracy of the steering mechanism. When properly oriented, the left and right faces of the lead spring 80 lie in a plane that is generally parallel to the axis about which the cam wheel 22 rotates. Stated differently, when the user holds the handle assembly 12 in a horizontal plane, the left and right faces of lead spring 80 lie in a vertical plane.

In accordance with a preferred embodiment, tab 81 is sized to fit within the distal end of tube body 62 with a tight friction fit. The fit is close enough to prevent rotation of spring 80 within guide tube body during actuation of the steering mechanism. If it is desired to further secure lead spring 80 to guide tube body 62, this may be accomplished, as desired, by soldering, brazing, welding, adhesives, etc.

The right and left steering wires 56 and 58 are soldered to the right and left faces of lead spring 80. When pulled by left rotation of the cam wheel 22, the left steering wire 56 bends the lead spring 80 to the left. When pulled by rightward rotation of the cam wheel 22, the right steering wire 58 bends the main lead spring 80 to the right. When pulled by leftward rotation of the cam wheel 22, the left steering wire 56 bends the main lead spring 80 to the left.

In the illustrated embodiment, the stiffness of the main lead spring 80 is not uniform, but varies along its length. Its stiffest point is near its proximal end region, where it is of its greatest width. Its stiffness is least at the tip end 88 of the shoulder 82. By varying the stiffness of the lead spring 80 between its proximal end and its distal tip end 88, the base of the electrode tip assembly 16 (where it joins the guide tube assembly 14) resists bending and buckling. The bending forces generated by the steering wires 56 and 58 are directed toward the distal tip end 88 of the main lead spring 80. The variable stiffness of the main lead spring 80 produced by progressively decreasing its width concentrates the bending forces at the distal tip end 82 of the electrode tip assembly 16.

Figure 5:
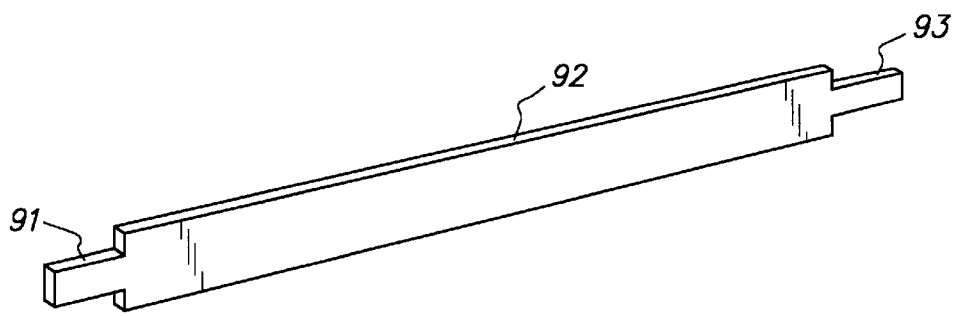
FIGS. 5 through 8 are perspective views of alternative steering springs in accordance with further embodiments the invention.

There are various alternative ways to vary the stiffness of the lead spring along its length. One alternative way shown in FIG. 4 is to vary both the width and thickness of the lead spring 90 so that both are greatest at the proximal end of the spring and least at its distal end. In the further alternative embodiment of FIG. 5, the width is uniform (except for end tabs 91 and 93) while the thickness decreases progressively from the proximal end of the spring to its distal end.

Figure 6:
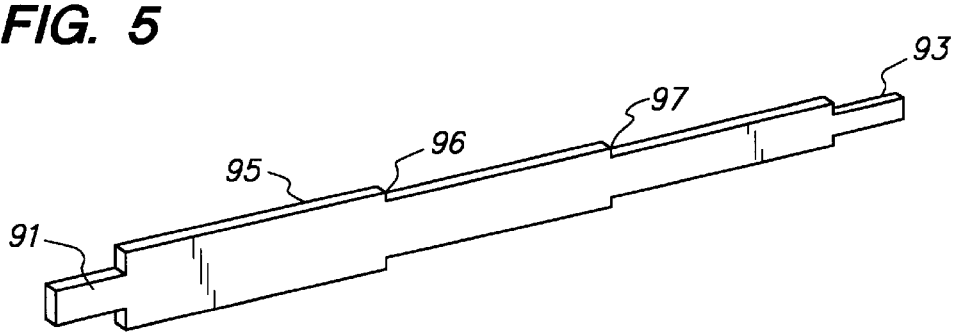

In the embodiment illustrated in FIG. 6, a still alternative way of varying the spring stiffness is shown. In this case a spring 95 is provided which has end tabs 91 and 93 of reduced width. The width of spring 95 is incrementally reduced in steps 96 and 97 (or a greater number of steps). This stepwise reduction in width achieves an effect similar to that of tapering the width or thickness of the spring.

Figure 7:
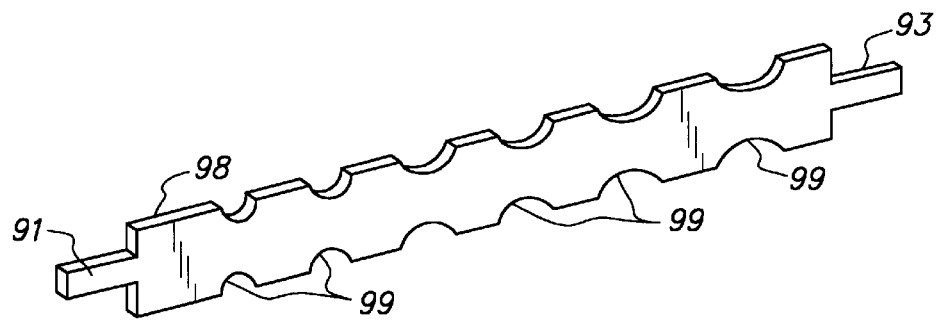
Figure 8:
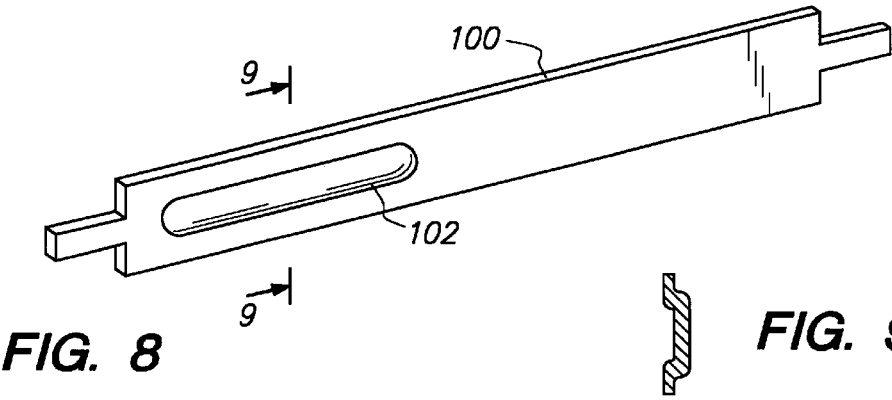
Figure 9:
FIG. 9 is a sectional view taken along Line 9—9 of FIG. 8.

In the still further embodiment shown in FIG. 7 an incremental variation in stiffness is provided by cutting notches 99 along the opposite edges of a uniform cross section spring. The frequency, width and depth of the notches is progressively varied to impart variable stiffness to the spring. In yet another variation shown in connection with spring 100 of FIGS. 8 and 9, the spring is provided with at least one dimple 102 which imparts stiffness and compression resistance to the proximal end of spring 100. The distal section of spring 100 is weaker and thus the bending and axial loads are transferred there.

The electrodes 17 and 19 are connected in conventional fashion by means of appropriate leads (not shown) to external energy sources, appropriate conventional catheter control equipment and monitoring equipment, usually through the lumen of body 62 and cable 48. Conducting wires also transfer radio frequency energy to the tip electrode 17 to carry out ablation procedures within the heart.

Methods for manufacturing catheter assemblies utilizing spring assemblies are described in the above referenced U.S. Pat. No. 5,363,861, which is incorporated by reference herein as if set forth in detail.

Various features of the invention are set forth in the following claims.

We claim:

1. A catheter steering mechanism, comprising:

a guide tube having a distal end;

a tip assembly carried by the distal end of the guide tube and including a variable stiffness spring being bendable in response to external forces, the variable stiffness spring having a proximal region attached to the guide tube at a point proximal to the distal end of the guide tube and a distal region that extends free of and beyond the distal end of the guide tube, the variable stiffness spring having a variable stiffness between its proximal and distal regions so that the proximal region is more resistant to bending than the distal region;

at least one steering wire attached to the variable stiffness spring beyond the distal end of the guide tube; and a controller attached to the steering wire for applying force to the steering wire to bend the spring beyond the distal end of the guide tube.

2. A catheter steering mechanism according to claim 1, wherein the variable stiffness spring has a uniform width and progressively decreases in thickness from its proximal region to its distal region.

3. A catheter according to claim 1 wherein said variable stiffness spring has a uniform thickness and progressively decreases in width from its proximal end to its distal end.

4. A catheter according to claim 1 wherein said variable stiffness spring progressively decreases in width and thickness from its proximal end to its distal end.

5. A catheter according to claim 3 wherein said width progressively decreases in stepped increments.

6. A catheter according to claim 1 wherein said variable stiffness spring progressively decreases in bending resistance from its proximal end to its distal end due to notches provided along at least one edge thereof.

7. A catheter according to claim 6 wherein said notches progressively increase in width and depth in a distal direction whereby the distal end of said variable stiffness spring is imparted with less bending resistance than the proximal end of said variable stiffness spring.

8. A catheter according to claim 1 wherein said variable stiffness spring decreases in bending resistance from its proximal end to its distal end due to at least one stiffening indentation provided therein.

9. A catheter steering mechanism according to claim 1, wherein the tip assembly carries an electrode.

10. A catheter steering mechanism, comprising:

a guide tube having a distal end;

a tip assembly carried by the distal end of the guide tube including
       a variable stiffness spring having a central plane and a stiffness and being bendable in response to external forces, the variable stiffness spring having a proximal region attached to of the guide tube at a point proximal to the distal end of the guide tube and a distal region that extends free of and beyond the distal end of the guide tube, the variable stiffness spring having a variable stiffness between its proximal and distal regions ends so that the proximal region end is more resistant to bending than the distal region, the proximal region further having a reduced width adapted to make a friction fit within the guide tube at a point proximal to the distal end of the guide tube, whereby the variable stiffness spring flexes perpendicularly to the central plane of the variable stiffness spring, at least one steering wire attached to the variable stiffness spring beyond the distal end of the guide tube, and a controller attached to the steering wire for applying a force to the steering wire to bend the variable stiffness spring beyond the distal end of the guide tube.

11. A catheter steering mechanism according to claim 1, wherein the proximal region of the variable stiffness spring is further secured to of the guide tube by means of brazing soldering, welding or an adhesive.

* * * * *